United States Patent [19]

Suzuki et al.

[11] Patent Number: 4,459,365

[45] Date of Patent: Jul. 10, 1984

[54] METHOD OF RECOVERING A CATALYTIC METAL

[75] Inventors: Takashi Suzuki; Kouichi Kitahara; Tomiyoshi Furuta; Sadao Nozaki, all of Niigata, Japan

[73] Assignee: Mitsubishi Gas Chemical Company, Inc., Tokyo, Japan

[21] Appl. No.: 379,446

[22] Filed: May 18, 1982

[30] Foreign Application Priority Data

May 29, 1981 [JP]  Japan .................................. 56-82342
Sep. 9, 1981 [JP]  Japan ................................. 56-141955

[51] Int. Cl.$^3$ ........................ B01J 37/06; B01J 37/00
[52] U.S. Cl. ..................................... 502/24; 502/31; 423/50; 562/414; 549/248
[58] Field of Search .................. 252/414, 420; 423/49, 423/138, 150, 50, 139; 562/414; 549/248; 502/24, 31

[56] References Cited

U.S. PATENT DOCUMENTS

| | | | |
|---|---|---|---|
| 2,680,757 | 6/1954 | Himel | 562/414 |
| 2,727,921 | 12/1955 | Taves | 562/414 |
| 3,465,013 | 9/1969 | Ichikawa et al. | 562/414 |
| 3,557,173 | 1/1971 | Trevillyan | 562/414 |
| 3,873,468 | 3/1975 | Kobinata et al. | 502/24 |
| 3,956,175 | 5/1976 | Shigeyasu et al. | 502/24 |
| 4,225,458 | 9/1980 | Huang et al. | 502/24 |
| 4,255,279 | 3/1981 | Spohn et al. | 502/24 |
| 4,298,759 | 11/1981 | Harper et al. | 423/139 |

FOREIGN PATENT DOCUMENTS

| | | | |
|---|---|---|---|
| 40-4820 | 3/1965 | Japan . | |
| 0741584 | 12/1955 | United Kingdom | 562/414 |
| 0892766 | 3/1962 | United Kingdom | 562/414 |
| 1094726 | 12/1967 | United Kingdom | 562/414 |

OTHER PUBLICATIONS

Dean, *Lange's Handbook of Chemistry*, 12th Ed., pp. 10-103 to 10-116, 1979, Ed., McGraw-Hill.

*Primary Examiner*—Delbert E. Gantz
*Assistant Examiner*—Lance Johnson
*Attorney, Agent, or Firm*—Armstrong, Nikaido, Marmelstein & Kubovcik

[57] ABSTRACT

A method of recovering a catalytic cobalt and/or manganese from a distillation residue in a process for preparing an aromatic carboxylic acid comprising a liquid-phase oxidation of the aromatic hydrocarbon having aliphatic substituent(s) or its oxidized derivatives in the presence of the catalytic cobalt and/or manganese and the distillation of the reaction product, which comprises successively or simultaneously treating the distillation residue with water and with an organic solvent having a relative dielectric constant D of $$3.0 \leq D \leq 35$$

9 Claims, No Drawings

METHOD OF RECOVERING A CATALYTIC METAL

This invention relates to a method of recovering a catalytic cobalt and/or manganese from a distillation residue obtained in a process for preparing an aromatic carboxylic acid which comprises oxidizing an aromatic hydrocarbon having aliphatic substituent(s) or its oxidized derivatives in liquid phase in the presence of the catalytic cobalt and/or manganese and distilling out the resulting aromatic carboxylic acid from the reaction product.

As processes for preparing aromatic carboxylic acid by the liquid phase oxidation of the corresponding alkylbenzene or its oxidized derivatives in a solvent such as acetic acid, water or the like in the presence of a heavy metal ion catalyst, there are known the process for preparing terephthalic acid from p-xylene or p-tolualdehyde, the process for preparing isophthalic acid from m-xylene, the process for preparing phthalic anhydride from o-xylene, the process for preparing trimellitic anhydride from pseudocumene or dimethylbenzaldehyde, the process for preparing pyromellitic anhydride from durene, and so on. In these processes and particularly in the processes for preparing phthalic anhydride, trimellitic anhydride and pyromellitic anhydride, distillation is often employed for separating the objective product from the oxidized reaction mixture. The method for separating aromatic carboxylic acid by distillation will be illustrated below by referring to the case of preparing trimellitic anhydride from pseudocumene as an example.

If pseudocumene is oxidized with air in acetic acid solvent by using cobalt and/or manganese and bromine as catalyst, trimellitic acid can be obtained. As an example of such a process, the process of Japanese Patent Kokai (Laid-Open) No. 2,932/81 can be referred to. The method for obtaining trimellitic anhydride from the slurry containing trimellitic acid formed by the reaction can roughly be classified into the following two methods.

According to the first method, the reaction mixture is cooled and separated by filtration by which the major part of trimellitic acid, not readily soluble in the above-mentioned solvent, is taken out as a cake. Then it is converted to anhydride by heating it and further it is distilled, whereby trimellitic anhydride is obtained. The major part of the catalyst metals remains dissolved in the mother liquor together with 10-20% of trimellitic acid. The mother liquor contains metals formed by corrosion and tarry organic matters, exercising an adverse effect on the reaction. If the whole quantity of the mother liquor is recycled into the oxidation reaction system, the tarry organic matters and the said metals are accumulated and have an adverse effect on the reaction. Therefore, it is necessary to separate trimellitic acid and recover the catalyst therefrom.

According to the second method, the reaction mixture is introduced into molten trimellitic anhydride either directly or after removal of solvent, where a molten mixture consisting of catalytic metals, reaction intermediate, reaction by-product and trimellitic anhydride is withdrawn as a bottom and a mixture composed mainly of solvent acetic acid and water is obtained as a distillate. The bottom is vacuum-distilled at a temperature of 180°–350° C. under a reduced pressure of 1–80 Torr, whereby trimellitic anhydride is obtained as distillate and catalytic metals, reaction intermediate and a part of trimellitic anhydride remains as a residue. The residue from which trimellitic anhydride has been removed by distillation contains the major part of catalytic metals which must also be recovered.

As a method for recovering catalytic metals from such distillation residue, the water extraction method is disclosed in U.S. Pat. No. 2,964,559. Though this method has a high catalytic metal recovery rate and is excellent both economically and from the viewpoint of process procedure, it is disadvantageous from the viewpoint of removing the tarry oxidized by-product and removing the metallic ions other than cobalt and manganese, such as iron, nickel and the like, formed by the corrosion of apparatuses. With the aim of removing such a disadvantage of water extraction method, the method for achieving the object by delicately controlling pH of water extract solution has been proposed (Japanese Patent Publication No. 14,637/74). However, this method has also a disadvantage that BOD increases because an alkaline substance is used in the process.

On the other hand, as a method for recovering metals substitutive for the water extraction method, the method of washing with organic solvent (Japanese Patent Publication No. 4,820/65) is known. According to this method, after filtering the reaction mixture, solvent and water formed by reaction are distilled off from the mother liquor and the residue is washed with an organic solvent to recover the insoluble heavy metal salts as a cake. Though this method is excellent in that it uses no alkaline substance, it is disadvantageous in that the recovery rate of heavy metals is somewhat low.

The present inventors have conducted elaborated studies on a method of recovering a catalytic cobalt and/or manganese from a distillation residue in a process for preparing an aromatic carboxylic acid comprising oxidation of an alkylbenzene in liquid phase in acetic acid solvent in the presence of the catalytic cobalt and/or manganese followed by separation of the resulting aromatic carboxylic acids from the reaction mixture by distillation. As the result, there were found surprising facts that, if the distillation residue is treated with water and then washed with a specified organic solvent, the heavy metals, almost completely soluble in organic solvent when the water treatment is not carried out, can hardly dissolve into the organic solvent and under some conditions its 90% or more is distributed in the cake, and that, if the distillation residue is washed with a specified aqueous organic solvent, the catalytic metals can be recovered in the cake in a high yield. Based on these findings, this invention was accomplished.

Thus, this invention consists in a method of recovering a catalytic cobalt and/or manganese from a distillation residue in a process for preparing an aromatic carboxylic acid comprising a liquid-phase oxidation of aromatic hydrocarbon having aliphatic substituents or its oxidized derivatives in the presence of the catalytic cobalt and/or manganese and distillation of the reaction product, which comprises successively or simultaneously treating the distillation residue with water and with an organic solvent. More particularly, this invention relates to said method of recovering a catalytic cobalt and/or maganese wherein the distillation residue is subjected to a hydration treatment and then washed with an organic solvent having a relative dielectric constant D of:

$$3.0 \leq D \leq 35$$

as well as to said method of recovering a catalytic cobalt and/or manganese wherein the distillation residue is washed with a mixed solution consisting of water and an organic solvent having a relative dielectric constant D falling in the range specified above. Although, in this invention, the reason why the heavy metal compounds change from a substance soluble in organic solvent to a substance insoluble in organic solvent is unknown, the fact that the hydration treatment is accompanied with a generation of heat and the hydration treatment causes an increase in weight (about 10%) of the distillation residue makes it consider that some hydration reaction takes place to decompose the chelate compound of heavy metal.

In this invention, the hydration treatment of the metallic catalyst-containing distillation residue can be completed sufficiently by only adding 0.01-10 times, based on the weight of distillation residue, of water to the distillation residue and then stirring the resulting mixture until it becomes pasty or slurry-like. This treatment can be carried out effectively, whether it is carried out at ordinary temperature or it is carried out with heating. A similar effect can also be obtained by blowing steam into the distillation residue. Various modes of practice can be selected from consideration of economy and workability of the whole processes.

Then, an organic solvent is added successively to the hydrated distillation residue to remove organic matters such as tarry by-product. Though the water added may be partially distilled off before the washing treatment with organic solvent, this distillation is not particularly necessary from the viewpoint of recovery rate of heavy metals.

Alternatively, the hydration treatment of the metallic catalyst-containing distillation residue can also be carried out by washing the residue simultaneously with water and the organic solvent in the form of a mixture in which water content based on the solvent is 1 to 20% by weight. If the water content is less than 1% or more than 20%, the dissolving loss of catalytic metal increases. In this method, the washing treatment with a mixture of water and organic solvent is carried out at ordinary temperature or with heating.

The organic solvent usable in this invention are those having a relative dielectric constant D falling in the following range:

$$3.0 \leq D \leq 35$$

Aliphatic hydrocarbons such as hexane, heptane and the like and aromatic hydrocarbons such as benzene, xylene, pseudocumene and the like have D value smaller than 3.0, and they are inappropriate because the solubility of tarry impurities in them is low. Some other substances having a D value greater than 35, such as dimethylformamide, are also inappropriate because they dissolve the metallic components. However, a mixture of dimethylformamide and a hydrocarbon such as pseudocumene which has been prepared by mixing them so that D of the mixture falls in the above-mentioned range can be used as the organic solvent of this invention. When D value is controlled by mixing different solvents in the above-mentioned manner, the D value of the mixture may be regarded as obeying the additive rule.

Examples of the organic solvent preferably usable in this invention include ketones such as acetone, methyl ethyl ketone, acetophenone and the like; esters such as methyl acetate, ethyl acetate, ethylbenzoate and the like; ethers such as ether, dioxane, trioxane, glyme and the like; and aldehydes such as acetaldehyde and the like; as well as 1:1 mixture of acetic acid and pseudocumene, 1:1 mixture of dimethylformamide and pseudocumene, and the like. Though dioxane is mentioned in literature to have a D value of 2.2, it actually exhibits a polarity comparable to that of other ethers, so that it is usable as the organic solvent of this invention. Accordingly, in this invention, relative dielectric constant D of dioxane is regarded as 5.86 and it is classified as a solvent falling in the scope of this invention. The organic solvent is used preferably in an amount of about 0.1-20 times the weight of distillation residue. If its amount is less than 0.1 time the weight of distillation residue, the removal of organic matter is insufficient. If it is greater than 20 times, the recovery of organic solvent becomes uneconomical.

As the mode of the washing with organic solvent, any methods hitherto known may be employed. Typically, the mode of mixing-sedimentation separation type can be referred to.

The temperature of the washing with solvent may be ordinary temperature or elevated temperature, and it may be appropriately selected with consideration of the boiling point of solvent used. As for the pressure, the method of this invention can be practised both under ordinary pressure and under elevated pressure.

According to this invention, the metal catalyst-containing cake is subjected to a hydration treatment and a treatment with organic solvent, or washed with a mixture of water and the organic solvent, and thereby impurities such as tar and the like, as well as the metallic components formed by corrosion such as iron, nickel, chromium and the like, can be removed by dissolution and catalytic metals can be recovered in cake insoluble in organic solvent, in a high recovery rate.

EXAMPLE 1

Into a batch reactor having a capacity of 30 liters were charged 5 kg of pseudocumene and 12.4 kg of acetic acid (containing 5% by weight of water), and they were reacted at a temperature of 120°-150° C. for 2.5 hours while blowing air thereinto. As the catalyst, a solution of 23 g of cobalt acetate tetrahydrate, 72 g of manganese acetate tetrahydrate and 132 g of hydrobromic acid dissolved in acetic acid was used. Throughout a reaction for 2.5 hours, 3.0 moles of oxygen was consumed per one mole of pseudocumene.

After completion of the batch reaction, the slurry was again oxidized in a flow reactor having an inner volume of 2 liters at a temperature of 220° C., under a pressure of 20 kg/cm² G, for a liquid residence time of 2 hours. The overall yield of trimellitic acid in the oxidation reaction was 85%. The slurry formed by the oxidation reaction was subjected to desolvation and dehydration in a flow dehydrating reactor having an inner volume of 0.5 liter at a temperature of 230° C., at ordinary pressure, for a liquid residence time of one hour. Thus, crude trimellitic anhydride containing the whole quantity of the catalytic heavy metals was obtained as a bottom.

The crude trimellitic anhydride was subjected to a batch distillation in a packed tower having a theoretical plate number of 0.8 to obtain trimellitic anhydride as a distillate. The conditions of the distillation were as follows: tower top pressure: 3.5 Torr, temperature: 210° C., temperature in still: 240° C.

Composition of the distillation residue was as shown in Table 1.

TABLE 1

| Component | % by weight |
|---|---|
| Trimellitic anhydride | 63.4 |
| Phthalic acids[*1] | 0.7 |
| Methylphthalic acids[*2] | 0.5 |
| Pyromellitic anhydride | 0.5 |
| Cobalt | 0.616 |
| Manganese | 1.94 |
| Others[*3] | Remainder |

[*1]A mixture composed mainly of terephthalic acid and isophthalic acid
[*2]A mixture of methylterephthalic acid and methylisophthalic acid
[*3]Tarry organic matter and so on are contained.

Into a test tube was introduced 0.7445 g of the distillation residue of Table 1, and was added about 15 ml of water. After boiling the mixture above the flame of a burner, it was transferred into a beaker together with 20 ml of washing water and concentrated with boiling to obtain a paste. The paste was dried at 90° C. for one hour under a reduced pressure of 100 Torr to obtain a dry solid. To the solid in the beaker was added 10.4 g of ethyl acetate, the mixture was thoroughly stirred with glass rod, and then it was filtered. The cake was washed with 15.7 g of ethyl acetate. The cake thus obtained was dried for one hour in an air oven kept at a temperature of 90° C. and a pressure of 100 Torr to obtain 0.2334 g of a dry cake. The concentrations of heavy metals in the cake and the filtrate were analyzed by atomic absorption method to find that the concentrations of cobalt and manganese in the cake were 1.98% and 4.65%, respectively, the concentrations of cobalt and manganese in the filtrate were 16.5 ppm and 1.9 ppm, respectively, and the concentrations of cobalt and manganese in the washings were 31.7 ppm and 3.1 ppm, respectively. These results means that the recovery rates of cobalt and manganese were 88.7% and 99.4%, respectively. The concentration of trimellitic acid in the cake was 29% by weight.

COMPARATIVE EXAMPLE 1

Into a 300 cc beaker was introduced 50.3 g of the same distillation residue as used in Example 1. Without carrying out hydration treatment, 104.9 g of ethyl acetate was poured and the mixture was stirred at ordinary temperature for one hour. The resulting slurry was filtered, and the cake was washed with 52.4 g of ethyl acetate.

The results of the experiment are shown in Table 2. By comparing the results of Table 2 with those of Example 1, it is understandable that the solubility difference between the case of carrying out hydration treatment and the case of carrying out no hydration treatment amounts to about 80 times with regard to cobalt and to 100 times or more with regard to manganese.

TABLE 2

| Weight of cake (g) | 2.12 |
|---|---|
| Co concentration in cake (%) | 5.42 |
| Co concentration in filtrate (ppm) | 1330[*1], 111[*2] |
| Mn concentration in cake (%) | 15.1 |
| Mn concentration in filtrate (ppm) | 4212[*1], 300[*2] |
| Recovery rate of Co (%) | 36.7 |
| Recovery rate of Mn (%) | 33.9 |

[*1]Filtrate
[*2]Washings

EXAMPLES 2 AND 3

First, the same distillation residue as used in Example 1 was subjected to a hydration treatment. Thus, 10.7 g of the distillation residue was sufficiently ground and introduced into a beaker, to which was added 10.0 g of water. After covering the beaker with a watch glass, the content of the beaker was concentrated with boiling for one hour until it became pasty. Then it was dried for 2.5 hours in an air oven kept at a temperature of 90° C. and a pressure of 100 Torr. Thus, 11.7 g of dry solid was obtained. Then, 5.46 g of the solid was washed with acetone, and 5.77 g was washed with methyl ethyl ketone. The results are shown in Table 3.

In the case of Example 2, 82% of the unidentified organic matter present in the distillation residue had been removed by the washing with acetone.

TABLE 3

| Organic solvent | | Example 2 Acetone | Example 3 MEK |
|---|---|---|---|
| Hydrate of distillation residue (g) | | 5.46 | 5.77 |
| Solvent (g) used | First time | 12.1 | 13.8 |
| | Washing | 25 | 25 |
| | Washing | 20 | |
| Dry cake (g) | | 0.74[*1] | 2.63[*2] |
| Co concentration in filtrate (ppm) | First time | 51 | 26.2 |
| | Washing | 30.7 | 15.2 |
| | Washing | 13.5 | |
| Mn concentration in filtrate (ppm) | First time | 65 | 19.2 |
| | Washing | 24.3 | 5.4 |
| | Washing | 2.4 | |
| Co concentration (% by wt.) in cake | | 3.93 | 1.29 |
| Mn concentration (% by wt.) in cake | | 10.7 | 3.82 |
| Recovery rate (%) of Co | | 95.6 | 98.1 |
| Recovery rate (%) of Mn | | 98.5 | 99.7 |

[*1]Trimellitic acid 33%, pyromellitic acid and the like 3.3%, water 8.2%, others 41%
[*2]Trimellitic acid 72%

EXAMPLE 4

A distillation residue subjected to hydration treatment by the same procedure as in Example 2 was boiled under reflux for one hour in methyl ethyl ketone and then it was filtered while it was hot. After boiling the cake again under reflux for 15 minutes, it was again filtered while it was hot. The results are shown in Table 4.

TABLE 4

| Organic solvent | | Hot MEK |
|---|---|---|
| Hydrated distillation residue (g) | | 5.26 |
| Solvent (g) used | 1st time | 18 |
| | 2nd time | 18 |
| Dry cake (g) | | 1.324 |
| Co concentration in filtrate (ppm) | 1st time | 24.2 |
| | 2nd time | 19.2 |
| Mn concentration in filtrate (ppm) | 1st time | 7.4 |
| | 2nd time | 6.8 |
| Co concentration (% by wt.) in cake | | 2.14 |
| Mn concentration (% by wt.) in cake | | 6.86 |
| Recovery rate (%) of Co | | 98.0 |
| Recovery rate (%) of Mn | | 99.8 |

COMPARATIVE EXAMPLE 2

The similar procedure as in Example 2 was repeated, except that the acetone was replaced by DMF. As the result, the whole quantity was dissolved, so that no cake was obtained.

EXAMPLE 5

A distillation residue subjected to a hydration treatment by the similar procedure as in Example 2 was washed at ordinary temperature with 1:1 mixture of glacial acetic acid and pseudocumene. The results are shown in Table 5.

TABLE 5

| Organic solvent | | Glacial acetic acid + Pseudocumene (51:49)*1 |
|---|---|---|
| Hydrated distillation residue (g) | | 2.83 |
| Solvent (g) used | 1st time | 10.7 |
| | 2nd time | 12.8 |
| Dry cake (g) | | 1.826 |
| Co concentration (ppm) in filtrate | 1st time | 18.0 |
| | 2nd time | 16.7 |
| Mn concentration (ppm) in filtrate | 1st time | 20.6 |
| | 2nd time | 24.6 |
| Co concentration (% by wt.) in cake | | 0.91 |
| Mn concentration (% by wt.) in cake | | 2.67 |
| Recovery rate (%) of Co | | 93.6 |
| Recovery rate (%) of Mn | | 96.9 |

*1Ratio by weight

COMPARATIVE EXAMPLES 3 AND 4

Using a distillation residue obtained under the similar oxidation reaction conditions, dehydration conditions and distillation conditions as in Example 1, the washing experiments with acetone and ethyl acetate were repeated, without carrying out the hydration treatment. The results are shown in Table 6.

EXAMPLE 6

Water was added to the distillation residue used in Comparative Example 3 at a ratio of 0.2 (by weight), and the resulting pasty substance was washed with acetone. The results are shown in Table 6.

TABLE 6

| | Comparative Example 3 | Comparative Example 4 | Example 6 |
|---|---|---|---|
| Organic solvent | Ethyl acetate | Acetone | Acetone |
| Distillation residue (g) | 4.76 | 4.98 | 5.13 |
| Hydration treatment | Not carried out | Not carried out | Carried out* |
| Water (g) used for hydration | — | — | 1.08 |
| Amount of solvent used (g) | 29.85 | 54.87 | 40.92 |
| Weight of cake (g) | 1.508 | 0.572 | 1.467 |
| Co concentration (ppm) in filtrate | 287 | 616 | 32.8 |
| Mn concentration (ppm) in filtrate | 694 | 1730 | 47.9 |
| Fe concentration (ppm) in filtrate | 17.7 | 18.7 | 9.7 |
| Ni concentration (ppm) in filtrate | 16.3 | 15.6 | 9.5 |
| Cr concentration (ppm) in filtrate | 2.9 or less | 2.3 or less | 2.6 or less |
| Co concentration (%) in cake | 2.32 | 3.04 | 3.28 |
| Mn concentration (%) in cake | 6.50 | 8.27 | 9.02 |
| Fe concentration (ppm) in cake | 279 | 381 | 467 |
| Ni concentration (ppm) in cake | 179 | 269 | 240 |
| Cr concentration (ppm) in cake | 74.7 | 77.6 | 99.2 |
| Recovery rate (%) of Co | 82.3 | 34.8 | 97.7 |
| Recovery rate (%) of Mn | 84.3 | 34.0 | 98.7 |
| Recovery rate (%) of Fe | 47.6 | 18.0 | 66.7 |
| Recovery rate (%) of Ni | 38.8 | 15.7 | 51.3 |
| Recovery rate (%) of Cr | 80.1 | 30.0 | 96.1 |

*The treatment was completed only by adding water at room temperature and stirring the mixture.

EXAMPLE 7

In a beaker was placed 3.692 g of the same distillation residue as used in Example 1, to which was added 18.5 g of methyl ethyl ketone containing 4% by weight of water. After stirring the mixture thoroughly, it was suction-filtered with a glass filter. The cake thus obtained was dried for one hour in an air oven kept at a temperature of 90° C. and a pressure of 100 Torr to obtain 0.762 g of a dry cake. Concentrations of heavy metals in the cake and the filtrate were analyzed by atomic absorption method to find that concentrations of cobalt and manganese in the cake were 2.84% and 9.03%, respectively, and concentrations of cobalt and manganese in the filtrate were 59.7 ppm and 129 ppm, respectively. These results mean that recovery rates of cobalt and manganese were 95.1% and 96.1%, respectively.

COMPARATIVE EXAMPLE 5

In a beaker was placed 10 g of the same distillation residue as used in Example 1, to which was added 50.5 g of methyl ethyl ketone. Then, the same procedure as in Example 7 was carried out to obtain 1.75 g of dry cake. Concentrations of cobalt and manganese in the cake were 2.78% and 8.83%, respectively, and concentrations of cobalt and manganese in the filtrate were 210 ppm and 603 ppm, respectively. These results mean that recovery rates of cobalt and manganese were 79% and 79.7%, respectively. From these results, the effect brought about by using an aqueous solvent is clearly understandable.

EXAMPLE 8

Into a shaking type autoclave was thrown 4.99 g of the same distillation residue was used in Example 1, to which was added 24.6 g of methyl ethyl ketone containing 4% by weight of water. The mixture was heated at 160° C. for one hour with shaking. After allowing the autoclave to cool, the content was suction-filtered with a glass filter and the cake was dried in an air oven kept at a temperature of 90° C. and a pressure of 100 Torr to obtain 1.09 g of a dry cake. Concentrations of cobalt and manganese in the cake were 2.74% and 8.7%, respectively, and concentrations of cobalt and manganese in the filtrate were 44 ppm and 76 ppm, respectively. These results mean that recovery rates of cobalt and manganese were 97.2% and 98%, respectively.

What is claimed is:

1. A method of recovering catalytic cobalt and/or manganese from a distillation residue obtained in a process for preparing (1) phthalic anhydride from o-xylene, (2) trimellitic anhydride from pseudocumene or dimethylbenzaldehyde, or (3) pyromellitic anhydride from durene, by a liquid phase oxidation in the presence of catalytic cobalt and/or manganese and distillation of the crude oxidation product, said method comprising successively or simultaneously subjecting said distillation residue to a hydration treatment with water to form a residue containing said cobalt and/or manganese and washing said residue with an organic solvent having a relative dielectric constant D of $$3.0 \leq D \leq 35$$

and selected from the group consisting of ketones, esters, ethers, aldehydes, a mixture of acetic acid and pseudocumene, and a mixture of dimethylformamide and pseudocumene and recovering said catalytic cobalt and/or manganese from said residue.

2. The method of recovering a catalytic cobalt and/or manganese according to claim 1, wherein the method comprises successively treating the distillation residue with water and then with the organic solvent.

3. The method of recovering a catalytic cobalt and/or manganese according to claim 2, wherein the water is used in an amount by weight of 0.01 to 10 times the amount by weight of the distillation residue and the organic solvent is used in an amount by weight of 0.1 to 20 times the amount by weight of the distillation residue.

4. The method of recovering a catalytic cobalt and/or manganese according to claim 1, wherein the method comprises simultaneously treating the distillation residue with water and with the organic solvent.

5. The method of recovering a catalytic cobalt and/or manganese according to claim 3, wherein the organic solvent containing 1 to 20% by weight of water is used in an amount by weight of 0.1 to 20 times the amount by weight of the distillation residue.

6. The method of recovering catalytic cobalt and/or manganese according to claim 1, wherein the ketone is selected from the group consisting of acetone, methyl ethyl ketone, and acetophenone.

7. The method of recovering catalytic cobalt and/or manganese according to claim 1, wherein the ester is selected from the group consisting of methyl acetate, ethyl acetate, and ethylbenzoate.

8. The method of recovering catalytic cobalt and/or manganese according to claim 1, wherein the ether is selected from the group consisting of diethyl ether, trioxane, and glyme.

9. The method of recovering catalytic cobalt and/or manganese according to claim 1, wherein the aldehyde is acetaldehyde.

* * * * *